United States Patent [19]

Mingozzi et al.

[11] Patent Number: 5,041,112

[45] Date of Patent: Aug. 20, 1991

[54] EXTERNAL SPLINT FOR THE TREATMENT OF FRACTURES OF THE LONG BONES OF LIMBS

[75] Inventors: Franco Mingozzi; Marco Mandrioli, both of Bologna, Italy

[73] Assignee: Citieffe S.r.l., Lippo Di Calderara Di Reno, Italy

[21] Appl. No.: 618,864

[22] Filed: Nov. 28, 1990

[30] Foreign Application Priority Data

Nov. 30, 1989 [IT] Italy .................................. 3738 A/89

[51] Int. Cl.⁵ .............................................. A61F 5/04
[52] U.S. Cl. .......................................... 606/54; 606/59
[58] Field of Search .................. 606/59, 53, 54, 55, 606/56, 57, 62; 128/87 R, 85

[56] References Cited

U.S. PATENT DOCUMENTS

| 2,238,870 | 4/1941 | Haynes | 606/59 |
| 4,312,336 | 1/1982 | Danieletto | 606/59 |
| 4,502,473 | 3/1985 | Harris | 606/59 |
| 4,570,625 | 2/1986 | Harris | 606/59 |
| 4,662,365 | 5/1987 | Gotzen | 606/59 |
| 4,944,743 | 7/1990 | Gotzen | 606/59 |

Primary Examiner—Robert A. Hafer
Assistant Examiner—Michael Brown
Attorney, Agent, or Firm—Guido Modiano; Albert Josif

[57] ABSTRACT

The external splint for the treatment of fractures of the long bones of limbs is composed of a tubular body which encloses a cylindrical cavity and has one end prismatically engaged in a seat of a box-like element, which is elongated transversely to the axis of the tubular body. The box-like element is coupled to the tubular body by means of a screw which is rotatably supported in the box-like element and is screwed in a threaded hole defined in the end along the axis of the seat. The screw is cannulated to allow the accommodation of a strain-gauge for monitoring the behavior of the splint. A support for supporting the nail-holder clamps are applied to the box-like element and to the tubular body so that it is possible to adjust them according to a total of three degrees of freedom.

8 Claims, 4 Drawing Sheets

EXTERNAL SPLINT FOR THE TREATMENT OF FRACTURES OF THE LONG BONES OF LIMBS

BACKGROUND OF THE INVENTION

The present invention relates to an external splint for the treatment of fractures of long bones of limbs.

External splints are for example described in the European publications nos. 153546 and 235138, in the U.S. pat. no. 4,312,336 and in the German publication no. 3527342. The monitoring of stresses in fracture sites is known from the German publications nos. 3722595 and 3912080 and from the European publications no. 135394 and 386912.

SUMMARY OF THE INVENTION

The technical aim of the present invention is to provide an external splint, in particular a unilateral one, which has monitoring means capable of measuring and evaluating the behavior of fractures during the healing process and of consequently varying the biomechanical performance of the splint to make it more adequate for the callification phase in progress.

This aim is achieved by a splint which is characterized in that it comprises a tubular body which defines a cylindrical cavity and has an end which prismatically engages a seat of a box-like element which is coupled to said body by means of a cannulated screw which is rotatably supported in said element and is screwed in a threaded hole defined in said end transversely to the axis of said cylindrical cavity, the actuation of said screw causing the movement of the tubular body in the seat of the box-like element, said cannulated screw accommodating a strain gauge for monitoring the behavior of the splint, a first supporting means for a first series of nail-holder clamps being coupled to said box-like element so that it can be orientated along two orthogonal axes, a second supporting means for a second series of nail-holder clamps being coupled in said cylindrical cavity of said tubular body so that said second supporting means can be adjusted along an axis which is substantially perpendicular to said two orthogonal axes.

BRIEF DESCRIPTION OF THE DRAWINGS

Further peculiarities of the invention will become apparent hereinafter with the aid of the accompanying drawings, wherein.

DESCRIPTION OF THE PREFERRED EMBODIMENTS

Figure 1:
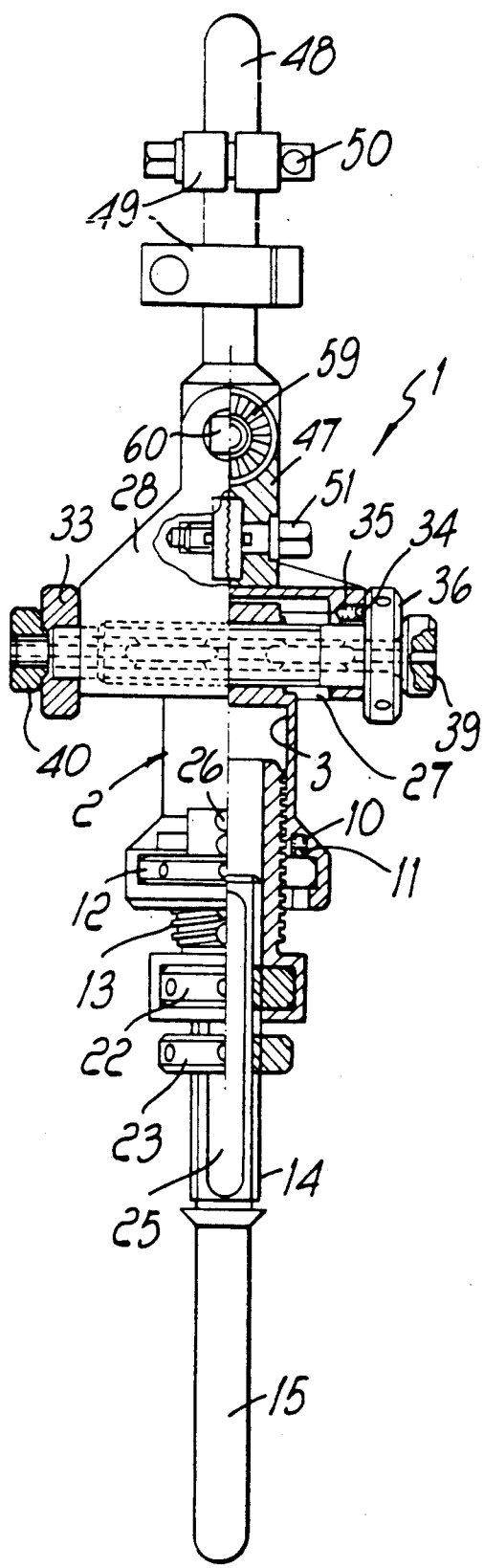
FIG. 1 is a partially sectional side view of a splint according to the invention in a preferred non limitative embodiment.
Figure 2:
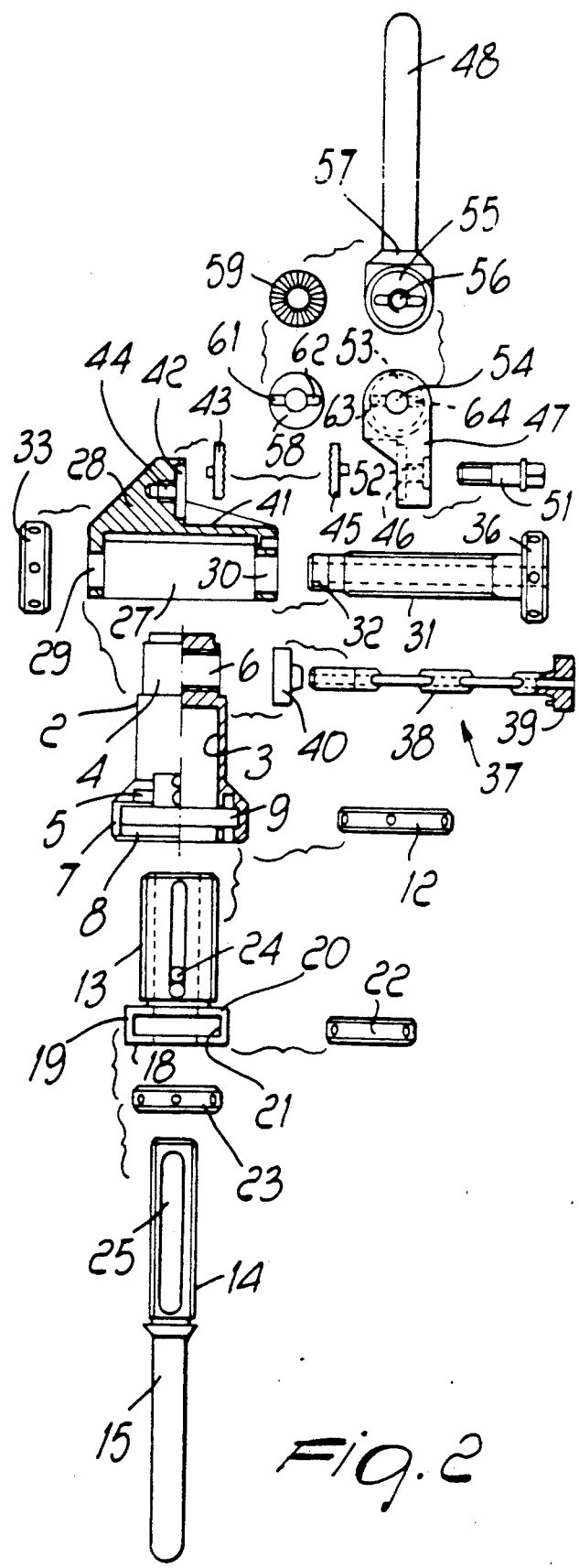
FIG. 2 is an exploded view, in a slightly reduced scale, of the splint of FIG. 1.
Figure 3:
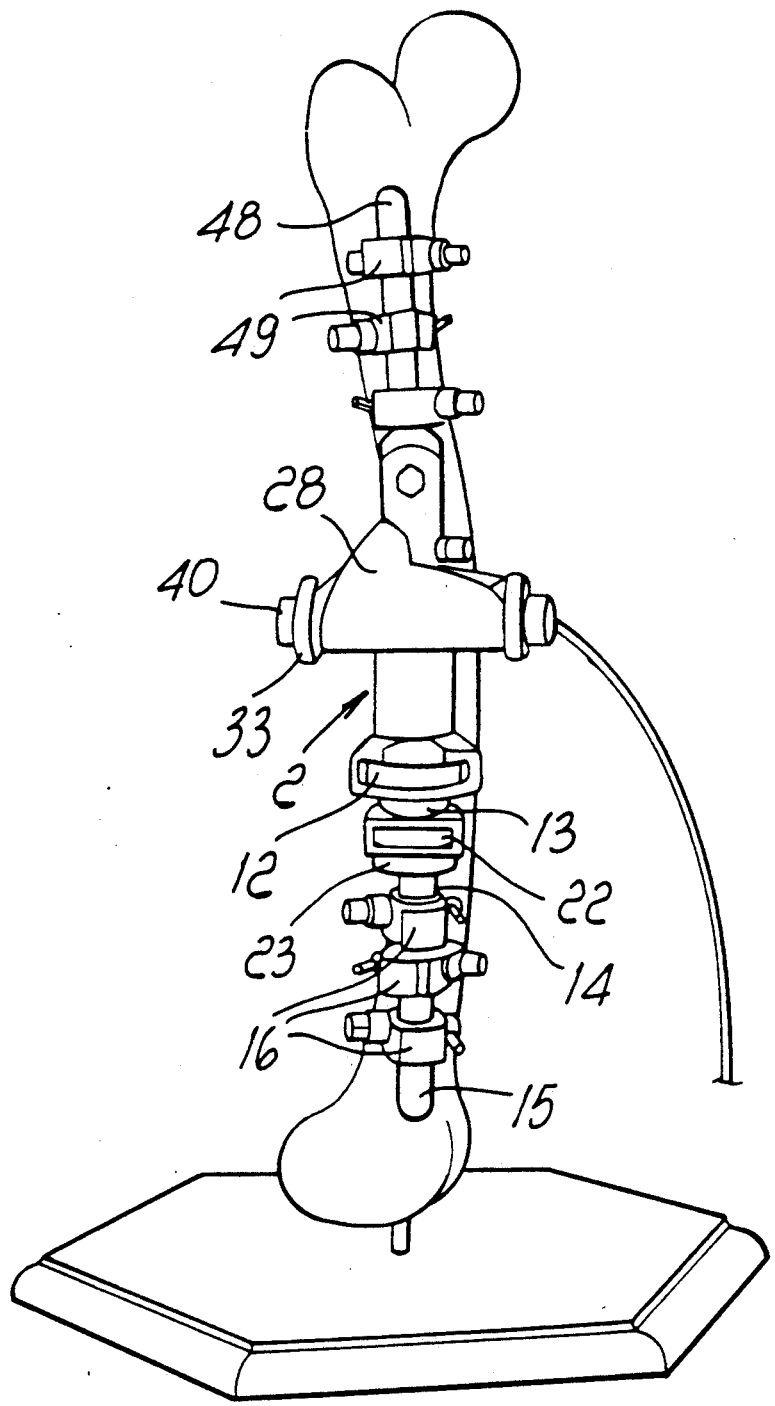
FIGS. 3, 4 and 5 are three views of the splint in use.
Figure 4:
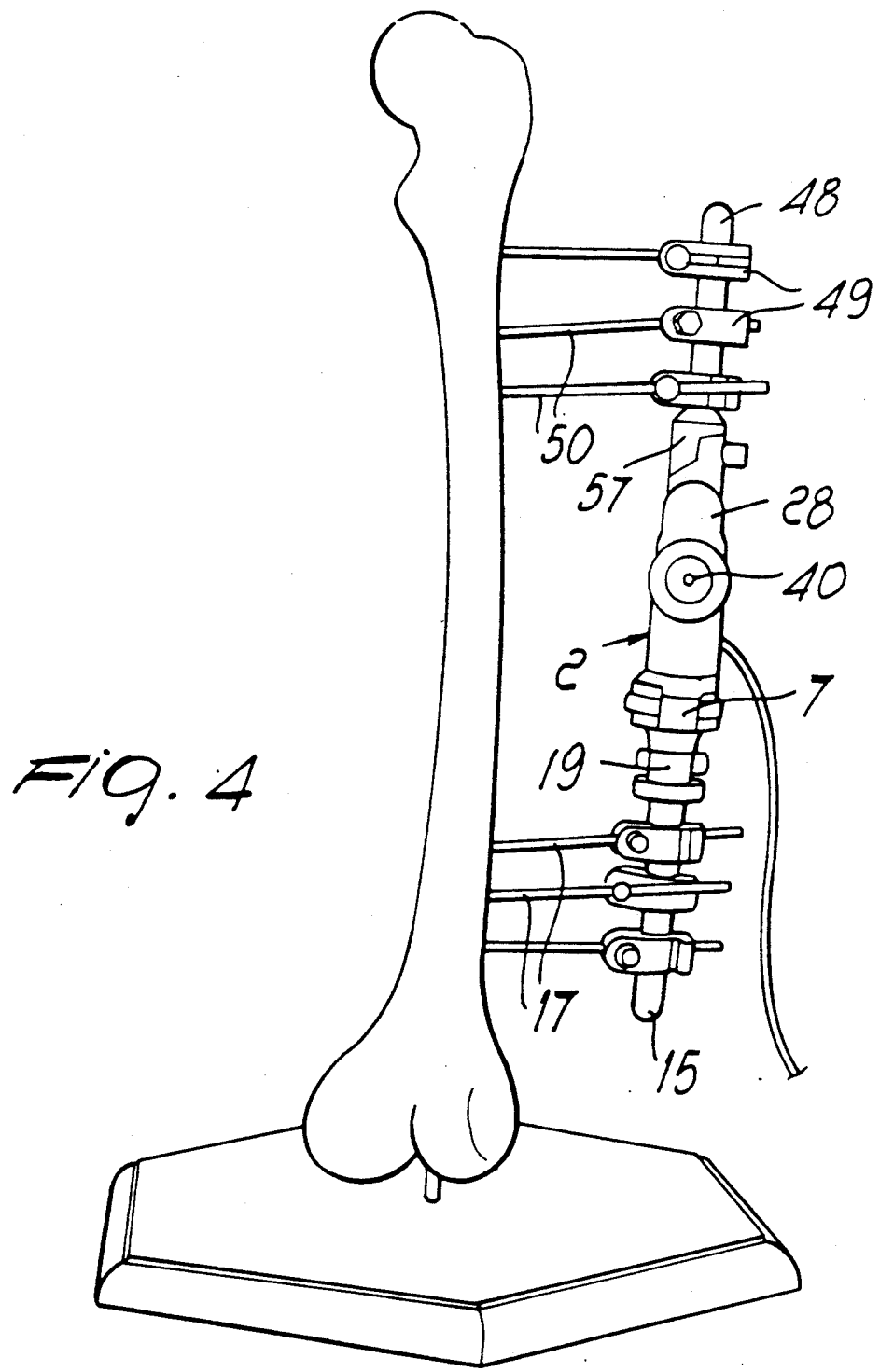
Figure 5:
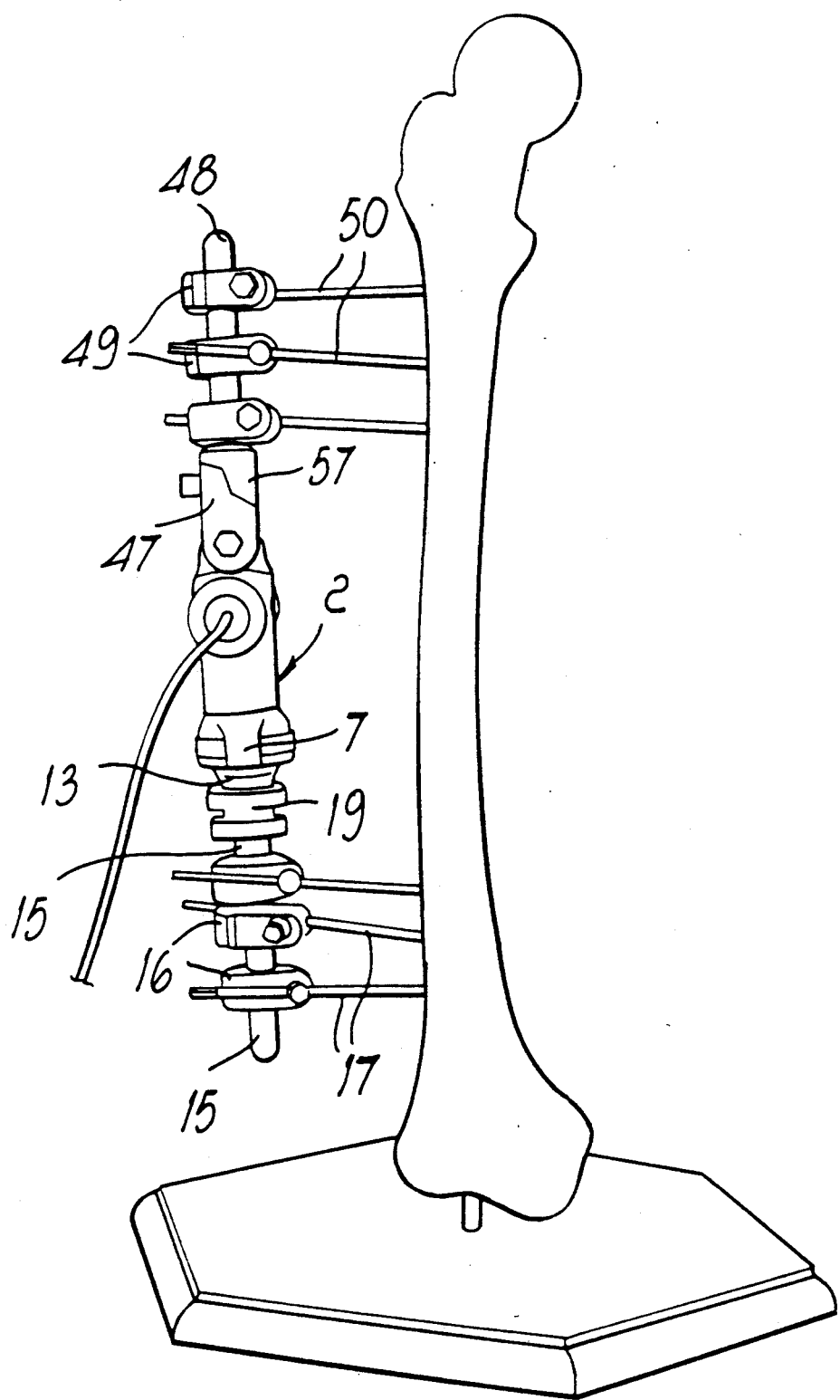

With reference to the above figures, the splint is generally indicated by the reference numeral 1 and comprises a tubular body 2 which is axially traversed by a cylindrical cavity 3 closed at one end and defines an annular expansion 5 at the opposite end, which is related to the opening of the cavity 3.

The head 4 is crossed by a threaded hole 6 diametrically with respect to the axis of the tubular body 2, and a ring 8 is arranged in front of the annular expansion 5, is connected thereto by two bridges 7 and defines a seat 9 together with the expansion.

A recess is provided in said expansion 5 and accommodates a spring 10 which acts on a ball 11 which is suitable for engaging one of a plurality of notches defined on a face of a ring 12 which is accommodated in the seat 9 and is screwed on a sleeve 13 which is inserted in the cavity 3. The ball 11 therefore rotationally locks the ring 12 in a given angular position.

The sleeve 13 preferably has an external square thread which allows to guide it in the cavity 3 and an internal thread in which the threaded tang 14 of a bar 15 is engaged; a plurality of clamps 16 for supporting the transosteal anchoring pins 17 (commonly termed "nails") is mounted on said bar 15.

In order to be able to axially position the tang 14 in the sleeve 13, said sleeve has, at the end outside the body 2, a ring 18 which, by means of tabs 19, is connected to a flange 20 of the sleeve 13 so as to define a seat 21 for a ring 22 which is engaged on the tang 14. The tang 14 is fixed with respect to the sleeve 13 by means of a counter-ring 23 which is suitable for acting against the ring 18 and/or by means of dowels 24 which are screwed in the sleeve 13 and are suitable for acting on a flattened portion 25 of the tang 14.

Similarly, the sleeve 13 is rotationally locked with respect to the tubular body 2 by means of dowels 26 which are screwed into the expansion 5 and act radially on the outer thread of the sleeve 13.

The head 4 is inserted in a seat 27 of a box-like element 28 which is coupled to the tubular body 2. The transverse section of the seat 27 is complementary to that of the head 4, and said seat is elongated in a direction which is perpendicular to the axis of the tubular body 2. In this manner, the head 4 can slide in the longitudinal direction of the seat 27 but provide a prismatic coupling between the box-like element 28 and the tubular body 2.

The box-like element 28 has two mutually coaxial openings 29, 30 at the opposite ends of the seat 27. A cannulated screw 31 is rotationally driven through the openings 29 and 30 and screwed in the hole 6, so as to provide the mechanical coupling between the tubular body 2 and the box-like element 28.

One end 32 of the screw 31 extends outside the opening 29, and a locking ring 33 is screwed thereon. A ball 34, stressed by a spring 35, is provided for the angular positioning of the screw 31, and both said ball 34 and said screw 31 are accommodated in a lateral recess of the box-like element 28. The ball 34 engages, similarly to what has been described above for the ball 11, a notch defined on the inner face of the head 36 of the screw 31. A strain-gauge 37 is accommodated inside the screw 31 and is connected to monitoring devices capable of analyzing and displaying the sensed data. The strain-gauge 37 is in practice an electromechanical transducer which comprises a central rod-like slotted portion 38 which is locked inside the screw 31 between a head 39 and a nut 40 which respectively abut on the head 36 of the screw and on the ring 33, as shown in FIG. 1.

The box-like element 28 has, on the opposite side with respect to the side on which the seat 27 opens, a recess 41 which defines, along a plane which is perpendicular to the axis of the screw 31, a circular depression 42 in which a washer 43, provided with a radial set of teeth on its outer face, is inserted. A threaded hole 44 is defined at the center of the depression 42.

An identical washer 45 is frontally coupled to the washer 43 and is accommodated in a corresponding circular depression 46 of a block 47 which acts as element for articulated coupling between the box-like element 28 and a bar 48 on which a plurality of clamps 49 for supporting a further series of "nails" 50 is mounted.

The block 47 is fixed to the box-like element 28 by means of a bolt 51 which is driven through a hole 52 which passes centrally through the depression 46 and the washers 45, 43 and engages in the threaded hole 44.

A depression 53 is furthermore provided in the block 47, has a central through hole 54 and is arranged along a plane which is perpendicular to that of the depression 46, whereas a further depression 55 with a central threaded hole 56 is defined at an enlarged end 57 of the bar 48. Respective washers 58, 59 are accommodated in the depressions 53 and 55, and their opposite faces have radial sets of teeth. A bolt 60, which is driven through the through hole 54 and the washers 58, 59, engages the threaded hole 56 and locks the bar 48 to the block 47.

It should be noted that the washers 43, 45 and 58, 59 have, on the side opposite to the toothed one, two diametrical ridges 61, 62 which, by engaging in corresponding notches 63, 64 defined on the bottom of the depressions 42, 46 and 53, 55, prevent the rotation of the washers, maintaining the mutual orientation of the block 47 with respect to the box-like element and of the bar 48 with respect to the block 47.

The described invention perfectly achieves the intended aim. It should be noted that the splint allows adjustment according to three degrees of freedom, and therefore perfect adaptation to the callification step of the fracture site. In particular, by acting on the bolts 51 and 60 it is possible to vary the orientation of the bar 48 with respect to the bar 15, whereas by screwing the ring 22 on the sleeve 13 and the threaded portion 14 in the sleeve 13 it is possible to set the distance between the clamps 16 and 49 and therefore between the nails 17 and 50. The actuation of the cannulated screw 31 furthermore allows to move the head 4 along the seat 27 and therefore to adjust the axis of the bar 15 with respect to the bar 48.

In particular, a fundamental prerogative of the present invention is constituted by the arrangement of the strain-gauge 37 in the cannulated screw 31 which, by acting as connecting element be&ween the box like element 28 and the tubular body 2, allows to detect the loads applied to the bone-splint system.

We claim:

1. External splint for the treatment of fractures of the long bones of limb, comprising a tubular body which defines a cylindrical cavity and has an end which prismatically engages a seat of a box-like element which is coupled to said body by means of a cannulated screw which is rotatably supported in said element and is screwed in a threaded hole defined in said end transversely to the axis of said cylindrical cavity, the actuation of said screw causing the movement of the tubular body in the seat of the box-like element, said cannulated screw accommodating a strain-gauge for monitoring the behavior of the splint, a first supporting means for a first series of nail-holder clamps being coupled to the box-like element so that it can be orientated along two orthogonal axes, a second supporting means for a second series of nail-holder clamps being coupled in said cylindrical cavity of said tubular body so that it can be adjusted along an axis which is substantially perpendicular to said two orthogonal axes.

2. Splint according to claim 1, wherein the tubular body defines, on the side opposite to the end which is prismatically engaged in said seat, an annular expansion in front of which ring is arranged said ring being connected to said expansion by a pair of bridges so as to define a seat for a ring which is screwed on the outer thread of a sleeve which is guided in said cylindrical cavity, said sleeve having an internal thread in which the threaded tang of a bar for the coupling of a plurality of clamps for supporting transosteal anchoring nails is engaged.

3. Splint according to claim 2, wherein the sleeve has, at the end which is external to the tubular body, a ring which is connected, by means of tabs, to a flange which is provided on the sleeve and defines a seat for a ring which is engaged on the threaded tang of the clamp-holder bar, a tang locking counter-ring being furthermore engaged on said tang.

4. Splint according to claim 2, comprising means for the angular positioning of the cannulated screw with respect to the box-like element and of the sleeve with respect to said tubular body, said means consisting of a ball which is loaded by a spring and is suitable for engaging one of a plurality of notches defined in the head of the cannulated screw and in the ring which is engaged on the outer thread of the sleeve.

5. Splint according to claim 2, further comprising dowels for fixing the sleeve in the cylindrical cavity of the tubular body and dowels for fixing the threaded tang of the clamp-holder bar in said sleeve.

6. Splint according to claim 1, wherein said box-like element has, at the opposite ends of the seat, two mutually coaxial openings through which said cannulated screw is rotatably driven, said box-like element being interposed between a head of said screw and a ring which is screwed on and end thereof driven outside said seat.

7. Splint according to claim 1, wherein said box-like element is connected to a respective clamp-holder bar by means of an articulation block which comprises coupling means suitable for allowing the angular positioning of the block with respect to the box-like element along an axis which is parallel to the cannulated screw and of the clamp-holder bar with respect to the block along an axis which is orthogonal to the preceding one.

8. Splint according to claim 7, wherein said coupling means comprises a first pair of adjacent washers arranged in depressions defined in the box-like element and in the articulation block and a second pair of adjacent washers arranged in depressions defined respectively in the articulation block and in an enlarged end of the clamp-holder bar, said paris of washers having opposite faces provided with radial sets of teeth which engage one another and rear faces provided with ridges which engage in respective notches of the depressions, two locking bolts being provided, said bolts being driven through said articulation block and the respective pairs of said washers, said bolts extending along said orthogonal axes.

* * * * *